(12) United States Patent
Kumar

(10) Patent No.: US 6,350,856 B1
(45) Date of Patent: Feb. 26, 2002

(54) CYTOKINE SUPPRESSIVE ANTI-INFLAMMATORY DRUG BINDING PROTEIN

(75) Inventor: Sanjay Kumar, King of Prussia, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/047,288

(22) Filed: Mar. 24, 1998

Related U.S. Application Data

(62) Division of application No. 08/802,191, filed on Feb. 18, 1997.

(51) Int. Cl.⁷ .................. C07K 1/00; C07K 14/00; A61K 38/02; A61K 45/00; C12P 21/00
(52) U.S. Cl. ................ 530/350; 424/85.1; 424/184.1; 435/69.1; 435/70.1; 514/2
(58) Field of Search .................. 530/350, 351; 424/85.1, 184.1, 185.1; 514/2, 8; 435/69.1, 70.1, 325, 320.1

(56) References Cited

U.S. PATENT DOCUMENTS

| | | | |
|---|---|---|---|
| 5,459,036 A | 10/1995 | Lechner et al. | 435/6 |
| 5,595,904 A | 1/1997 | Boulton et al. | 435/242 |
| 5,663,313 A | 9/1997 | Hawkins et al. | 536/238 |

FOREIGN PATENT DOCUMENTS

| | | |
|---|---|---|
| WO | WO9722704 | 6/1997 |
| WO | WO9744467 | 11/1997 |

OTHER PUBLICATIONS

Wang et al. Phosphorylation of the common neurotrophin receptor p75 by p38beta2 kinase affects NF–kappB and AP–1 activities. J. Molec. Neurosci. 15: 19–29, 2000.*

Lee et al. Inhibition of p38 MAP kinase as a therapeutic stategy. Immunopharmacol. 47: 185–201, 2000.*

Han et al. Molecular cloning of human p38 MAP kinase. Biochimica et Biophysica Acta 1265: 224–227, 1995.*

Stein et al. p38–2, a novel mitogen–activated protein kinase with distinct properties. J Biol Chem 272(31):19509–19517, 1997.*

Goedert et al. Activation of the novel stress–activated protein kinase SAPK4 by cytokines and cellular stresses is mediated by SKK3 (MKK6); comparison of its substrate specificity with that of other SAP kinases. EMBO J 16(12): 3563–3571, 1997.*

Han, Acc. No. U53442 (Jul. 30, 1996).

Tashima et al., Acc. No. U73142 (Oct. 22, 1996).

Han et al., Acc. No. U10871 (Aug. 19, 1994).

Higashitsagi, Acc. No. D83073 (Jan. 31, 1996).

Han et al., Acc. No. L35253 (Aug. 14, 1995).

Lechner et al., Acc. No. X79483 (Aug. 19, 1996).

Jiang et al., "Characterization of the Structure and Function of a new Mitogen–Activated Protein Kinase (P38BETA)", *Journal of Biological Chemistry*, 271(30), pp. 17920–17926 (Jul. 26, 1996).

Kumar et al., "Novel Homologues of CSBP/P38 Map Kinase Activation, Substrate Specificity and Sensitivity to Inhibition by Pyridinyl Imidazoles", *Biochemical and Biophysical Research Communications*, 235, pp. 533–538 (Jun. 26, 1997).

\* cited by examiner

*Primary Examiner*—Christine J. Saoud
*Assistant Examiner*—Bridget E. Bunner
(74) *Attorney, Agent, or Firm*—William T. Han; Ratner & Prestia; William T. King

(57) ABSTRACT p38beta2 polypeptides and polynucleotides and methods for producing such polypeptides by recombinant techniques are disclosed. Also disclosed are methods for utilizing p38beta2 polypeptides and polynucleotides in the design of protocols for the treatment of central nervous system disorder such as senile dementia of the Alzheimer's type (SDAT), multiple sclerosis, cerebral malaria, stroke, head trauma and spinal cord injury; cardiovascular diseases such as restenosis and atherosclerosis; inflammatory diseases such as Adult Respiratory Disease Syndrome (ARDS), Rheumatoid arthritis, Osteoarthritis, Inflammatory Bowel Disease (IBD), psoriasis, dermatitis, asthma; and other such diseases or conditions associated with dysregulated or excess cytokines such as osteoporosis, sepsis due to surgical or traumatic incident, chronic renal failure, AIDs, cachexia and autoimmune conditions such as lupus erthyromatosis, host graft rejection and graft versus host disease, among others, and diagnostic assays for such conditions.

4 Claims, 2 Drawing Sheets

Nucleotide and Amino Acid sequences from a p38beta2 (SEQ ID NOS: 1 and 2, respectively)

```
CCGGACATGTCGGGCCCTCGCGCCGGCTTCTACCGGCAGGAGCTGAACAAGACCGTGTGG    60
       M  S  G  P  R  A  G  F  Y  R  Q  E  L  N  K  T  V  W
GAGGTGCCGCAGCGGCTGCAGGGGCTGCGCCCGGTGGGCTCCGGCGCCTACGGCTCCGTC   120
 E  V  P  Q  R  L  Q  G  L  R  P  V  G  S  G  A  Y  G  S  V
TGTTCGGCCTACGACGCCCGGCTGCGCCAGAAGGTGGCGGTGAAGAAGCTGTCGCGCCCC   180
 C  S  A  Y  D  A  R  L  R  Q  K  V  A  V  K  K  L  S  R  P
TTCCAGTCGCTGATCCACGCGCGCAGAACGTACCGGGAGCTGCGGCTGCTCAAGCACCTG   240
 F  Q  S  L  I  H  A  R  R  T  Y  R  E  L  R  L  L  K  H  L
AAGCACGAGAACGTCATCGGGCTTCTGGACGTCTTCACGCCGGCCACGTCCATCGAGGAC   300
 K  H  E  N  V  I  G  L  L  D  V  F  T  P  A  T  S  I  E  D
TTCAGCGAAGTGTACTTGGTGACCACCCTGATGGGCGCCGACCTGAACAACATCGTCAAG   360
 F  S  E  V  Y  L  V  T  T  L  M  G  A  D  L  N  N  I  V  K
TGCCAGGCGCTGAGCGACGAGCACGTTCAATTCCTGGTTTACCAGCTGCTGCGCGGGCTG   420
 C  Q  A  L  S  D  E  H  V  Q  F  L  V  Y  Q  L  L  R  G  L
AAGTACATCCACTCGGCCGGGATCATCCACCGGGACCTGAAGCCCAGCAACGTGGCTGTG   480
 K  Y  I  H  S  A  G  I  I  H  R  D  L  K  P  S  N  V  A  V
AACGAGGACTGTGAGCTCAGGATCCTGGATTTCGGGCTGGCGCGCCAGGCGGACGAGGAG   540
 N  E  D  C  E  L  R  I  L  D  F  G  L  A  R  Q  A  D  E  E
ATGACCGGCTATGTGGCCACGCGCTGGTACCGGGCACCTGAGATCATGCTCAACTGGATG   600
 M  T  G  Y  V  A  T  R  W  Y  R  A  P  E  I  M  L  N  W  M
CATTACAACCAAACAGTGGATATCTGGTCCGTGGGCTGCATCATGGCTGAGCTGCTCCAG   660
 H  Y  N  Q  T  V  D  I  W  S  V  G  C  I  M  A  E  L  L  Q
GGCAAGGCCCTCTTCCCGGGAAGCGACTACATTGACCAGCTGAAGCGCATCATGGAAGTG   720
 G  K  A  L  F  P  G  S  D  Y  I  D  Q  L  K  R  I  M  E  V
```

The Figure

```
GTGGGCACACCCAGCCCTGAGGTTCTGGCAAAAATCTCCTCGGAACACGCCCGGACATAT  780
 V   G   T   P   S   P   E   V   L   A   K   I   S   S   E   H   A   R   T   Y
ATCCAGTCCCTGCCCCCCATGCCCCAGAAGGACCTGAGCAGCATCTTCCGTGGAGCCAAC  840
 I   Q   S   L   P   P   M   P   Q   K   D   L   S   S   I   F   R   G   A   N
CCCCTGGCCATAGACCTCCTTGGAAGGATGCTGGTGCTGGACAGTGACCAGAGGGTCAGT  900
 P   L   A   I   D   L   L   G   R   M   L   V   L   D   S   D   Q   R   V   S
GCAGCTGAGGCACTGGCCCACGCCTACTTCAGCCAGTACCACGACCCCGAGGATGAGCCA  960
 A   A   E   A   L   A   H   A   Y   F   S   Q   Y   H   D   P   E   D   E   P
GAGGCCGAGCCATATGATGAGAGCGTTGAGGCCAAGGAGCGCACGCTGGAGGAGTGGAAG 1020
 E   A   E   P   Y   D   E   S   V   E   A   K   E   R   T   L   E   E   W   K
GAGCTCACTTACCAGGAAGTCCTTAGCTTCAAGCCCCCAGAGCCACCGAAGCCACCTGGC 1080
 E   L   T   Y   Q   E   V   L   S   F   K   P   P   E   P   P   K   P   P   G
AGCCTGGAGATTGAGCAGTGAGGTGCTGCCCAGCAGCCCCTGAGAGCCTGTGGAGGGGCT 1140
 S   L   E   I   E   Q   *
TGGGCCTGCACCCTTCCACAGCTGGCCTGGTTTCCTCGAGAGGCACCTCCCACACTCCTA 1200
TGGTCACAGACTTCTGGCCTAGGACCCCTCGCCTTCAGGAGAATCTACACGCATGTATGC 1260
ATGCACAAACATGTGTGTACATGTGCTTGCCATGTGTAGGAGTCTGGGCA           1310
```

The Figure cont'd

SEQUENCE LISTING

<160> NUMBER OF SEQ ID NOS: 4

<210> SEQ ID NO 1
<211> LENGTH: 1310
<212> TYPE: DNA
<213> ORGANISM: HOMO SAPIENS

<400> SEQUENCE: 1

```
ccggacatgt cgggccctcg cgccggcttc taccggcagg agctgaacaa gaccgtgtgg      60
gaggtgccgc agcggctgca ggggctgcgc ccggtgggct ccggcgccta cggctccgtc     120
tgttcggcct acgacgcccg gctgcgccag aaggtggcgg tgaagaagct gtcgcgcccc     180
ttccagtcgc tgatccacgc gcgcagaacg taccgggagc tgcggctgct caagcacctg     240
aagcacgaga acgtcatcgg gcttctggac gtcttcacgc cggccacgtc catcgaggac     300
ttcagcgaag tgtacttggt gaccaccctg atgggcgccg acctgaacaa catcgtcaag     360
tgccaggcgc tgagcgacga gcacgttcaa ttcctggttt accagctgct gcgcgggctg     420
aagtacatcc actcggccgg gatcatccac cgggacctga gcccagcaa cgtggctgtg     480
aacgaggact gtgagctcag gatcctggat ttcgggctgg cgcgccaggc ggacgaggag     540
atgaccggct atgtggccac gcgctggtac cgggcacctg agatcatgct caactggatg     600
cattacaacc aaacagtgga tatctggtcc gtgggctgca tcatggctga gctgctccag     660
ggcaaggccc tcttcccggg aagcgactac attgaccagc tgaagcgcat catggaagtg     720
gtgggcacac ccagccctga ggttctggca aaaatctcct cggaacacgc ccggacatat     780
atccagtccc tgcccccccat gccccagaag gacctgagca gcatcttccg tggagccaac     840
cccctggcca tagacctcct tggaaggatg ctggtgctgg acagtgacca gagggtcagt     900
gcagctgagg cactggccca cgcctacttc agccagtacc acgacccga ggatgagcca      960
gaggccgagc catatgatga gagcgttgag gccaaggagc gcacgctgga ggagtggaag    1020
gagctcactt accaggaagt ccttagcttc aagcccccag agccaccgaa gccacctggc    1080
agcctggaga ttgagcagtg aggtgctgcc cagcagcccc tgagagcctg tggaggggct    1140
tgggcctgca cccttccaca gctggcctgg tttcctcgag aggcacctcc cacactccta    1200
tggtcacaga cttctggcct aggacccctc gccttcagga gaatctacac gcatgtatgc    1260
atgcacaaac atgtgtgtac atgtgcttgc catgtgtagg agtctgggca                1310
```

<210> SEQ ID NO 2
<211> LENGTH: 364
<212> TYPE: PRT
<213> ORGANISM: HOMO SAPIENS

<400> SEQUENCE: 2

```
Met Ser Gly Pro Arg Ala Gly Phe Tyr Arg Gln Glu Leu Asn Lys Thr
 1               5                  10                  15

Val Trp Glu Val Pro Gln Arg Leu Gln Gly Leu Arg Pro Val Gly Ser
             20                  25                  30

Gly Ala Tyr Gly Ser Val Cys Ser Ala Tyr Asp Ala Arg Leu Arg Gln
         35                  40                  45

Lys Val Ala Val Lys Lys Leu Ser Arg Pro Phe Gln Ser Leu Ile His
     50                  55                  60

Ala Arg Arg Thr Tyr Arg Glu Leu Arg Leu Leu Lys His Leu Lys His
 65                  70                  75                  80
```

-continued

```
Glu Asn Val Ile Gly Leu Leu Asp Val Phe Thr Pro Ala Thr Ser Ile
                 85                  90                  95
Glu Asp Phe Ser Glu Val Tyr Leu Val Thr Thr Leu Met Gly Ala Asp
            100                 105                 110
Leu Asn Asn Ile Val Lys Cys Gln Ala Leu Ser Asp Glu His Val Gln
            115                 120                 125
Phe Leu Val Tyr Gln Leu Leu Arg Gly Leu Lys Tyr Ile His Ser Ala
        130                 135                 140
Gly Ile Ile His Arg Asp Leu Lys Pro Ser Asn Val Ala Val Asn Glu
145                 150                 155                 160
Asp Cys Glu Leu Arg Ile Leu Asp Phe Gly Leu Ala Arg Gln Ala Asp
                165                 170                 175
Glu Glu Met Thr Gly Tyr Val Ala Thr Arg Trp Tyr Arg Ala Pro Glu
            180                 185                 190
Ile Met Leu Asn Trp Met His Tyr Asn Gln Thr Val Asp Ile Trp Ser
            195                 200                 205
Val Gly Cys Ile Met Ala Glu Leu Leu Gln Gly Lys Ala Leu Phe Pro
210                 215                 220
Gly Ser Asp Tyr Ile Asp Gln Leu Lys Arg Ile Met Glu Val Val Gly
225                 230                 235                 240
Thr Pro Ser Pro Glu Val Leu Ala Lys Ile Ser Ser Glu His Ala Arg
                245                 250                 255
Thr Tyr Ile Gln Ser Leu Pro Pro Met Pro Gln Lys Asp Leu Ser Ser
            260                 265                 270
Ile Phe Arg Gly Ala Asn Pro Leu Ala Ile Asp Leu Leu Gly Arg Met
        275                 280                 285
Leu Val Leu Asp Ser Asp Gln Arg Val Ser Ala Ala Glu Ala Leu Ala
            290                 295                 300
His Ala Tyr Phe Ser Gln Tyr His Asp Pro Glu Asp Glu Pro Glu Ala
305                 310                 315                 320
Glu Pro Tyr Asp Glu Ser Val Glu Ala Lys Glu Arg Thr Leu Glu Glu
                325                 330                 335
Trp Lys Glu Leu Thr Tyr Gln Glu Val Leu Ser Phe Lys Pro Pro Glu
            340                 345                 350
Pro Pro Lys Pro Pro Gly Ser Leu Glu Ile Glu Gln
        355                 360
```

<210> SEQ ID NO 3
<211> LENGTH: 19
<212> TYPE: DNA
<213> ORGANISM: HOMO SAPIENS

<400> SEQUENCE: 3
gtgaaattct gctccggac                                              19

<210> SEQ ID NO 4
<211> LENGTH: 33
<212> TYPE: PRT
<213> ORGANISM: HOMO SAPIENS

<400> SEQUENCE: 4

-continued

```
Ala Thr Cys Thr Cys Gly Ala Gly Ala Ala Gly Cys Thr Thr Thr Gly
 1               5                  10                 15

Cys Cys Cys Ala Gly Ala Cys Thr Cys Cys Thr Ala Cys Ala Cys Ala
            20                  25                  30

Thr
```

CYTOKINE SUPPRESSIVE ANTI-INFLAMMATORY DRUG BINDING PROTEIN

This is a divisional of application Ser. No. 08/802,191 filed Feb. 18, 1997.

FIELD OF INVENTION

This invention relates to newly identified polynucleotides, polypeptides encoded by them and to the use of such polynucleotides and polypeptides, and to their production. More particularly, the polynucleotides and polypeptides of the present invention relate to CSBP/p38 MAP Kinases family, hereinafter referred to as p38beta2. The invention also relates to inhibiting or activating the action of such polynucleotides and polypeptides.

BACKGROUND OF THE INVENTION

Cytokines play an important role in regulating the cellular response during inflammation and other immune functions. Of particular interest are the cytokines interleukin-1 (IL-1, $\alpha$ and $\beta$) and tumor necrosis factor (TNF, $\alpha$ and $\beta$), which are the intercellular proteins involved in the initial step of the inflammatory response cascade (Arai, et al., Ann. Rev. Biochem. 59: 783–836 (1990). Thus, there has been a substantial amount of research recently devoted to interfering with the production of IL-1 and TNR in response to an inflammatory stimulus.

One therapeutic approach involves suppressing the production of IL-1 and TNF at the level of transcription and/or translation and/or secretion. The activities associated with certain of pyridinyl imidazoles led to a class of compounds referred to as "CSAIDs", or Cytokine Suppressing Anti-Inflammatory Drugs. These compounds appear to arrest the expression of IL-1 and TNF predominantly at the translational level, although a lesser effect on transcription has also been observed but effects on other steps cannot be ruled out.

The pyridinyl imidazole, 5-(4-pyridyl)-6(4-flurophenyl)-2,3-dihydroimidazo(2,1-b)thiazole (SK&F 86002) was identified as the prototypic CSAID. The basis for its activity has been established and characterized (Lee, et al., Int'l. J. Immunopharm. 10(7): 835–843 (1988); Agents and Actions 27(¾): 277–279 (1989) and Int'l. J. Immunother. 6(1): 1–12 (1990)). SAR studies suggest that cytokine suppressive effect of the pyridinyl imidazoles represents a unique activity independent of their inhibitory effects on eicosanoid and leukotriene production.

Since the CSAIDs have substantial potential as novel anti-inflammatory therapeutic agents, there is significant interest in characterizing their mechanism of action at the molecular level, as well as obtaining compounds with increased selectivity and potency. Specifically, identification and characterization of the CSAID molecular target would enhance the understanding of the biochemical processes involved in inflammation and aid in the design and screening of more potent anti-inflammatory drugs. This invention discloses, inter alia, the purification and characterization CSAID binding proteins (CSBPs).

p38beta2 is a member of the CSBP/p38 MAP kinase family (Cytokine Suppressive Anti-Inflammatory Drug (CSAID) binding protein family) of serine-threonine protein kinases (Marshall, C. J. (1994) Curr. Opinion Genet. Develop. 4, 82–89). Members of the MAP kinase family are characterized by having a "TxY"amino acid motif (T=Threonine, Y=tyrosine and X is any amino acid) in an activation loop near to the active site. Phosphorylation of both the tyrosine and threonine by a MAP kinase kinase in response to an appropriate stimulus is required for the activation of MAP kinase activity. These are three families of MAP kinases which are distinguished by the nature of the "x" amino acid and the size of the activation loop (Cano, E., and Mahadevan, L. C. (1995) Trends Biochem. Sci 20, 117–122). Hence, the erks have TEY, JNK/SAPKs have TPY and the CSBP/p38s have TCY. These differences reflect differences in the activating MAP kinase kinases and in the cellular stimuli which activate each MAP kinase. Within each family, the activating stimuli appear to be very similar. Thus the erks respond mostly to mitogenic stimuli (e.g., EGF, PDGF), while the JNK/SAPKs and CSBP/p38s respond to several cellular stresses (eg UV, osmotic, heat or chemical stress, hypoxia ,oxidants etc) and prionflammatory stimuli (e.g., LPS, IL-1, TNF, etc.).

Recently, several new forms of P38 have been identified. In addition to the two splice variants of P38, CSBP1 and CSBP2, a further spliced variant was identified through a yeast two-hybrid interaction screen with the nuclear protein Max (Zervos, A. S. Faccio, L., Gatto, J. P., Kyriakis, J. M., and Brent, R. (1995) Proc. Natl. Acad. Sci. USA 92, 10531–10534). Two homologous with significant amino acid identity which also retain the "TCY" motif characteristic of the P38 family were also recently identified: p38beta (Jiang, Y., Chen, C., Li, Z., Guo, W., Gegner, J. A., Lin, S., and Han, J. (1996) J. Biol. Chem. 271, 17920–17926), and ERK6/SAPK3 (Lechner, C., Zahalka, M. A., Giot, J.-F., Moller, N. P. H., and Ullrich, A. (1996) Proc. Natl. Acad. Sci. USA 93, 4355–4359; Mertens, S., Craxton, M., and Goedert, M. (1996) FEBS lett., 383(3):273–6). This indicates that these CSBP/p38 MAP Kinases have an established, proven history as therapeutic targets. Clearly there is a need for identification and characterization of further members of CSBP/p38 MAP Kinases family which can play a role in preventing, amelioraing or correcting dysfunctions or diseases, including, but not limited to, central nervous system disorder such as senile dementia of the Alzheimer's type (SDAT), multiple sclerosis, cerebral malaria, stroke, head trauma and spinal cord injury; cardiovascular diseases such as restenosis and atherosclerosis; inflammatory diseases such as Adult Respiratory Disease Syndrome (ARDS), Rheumatoid arthritis, Osteoarthritis, Inflammatory Bowel Disease (IBD), psoriasis, dermatitis, asthma; and other such diseases or conditions associated with dysregulated or excess cytokines such as osteoporosis, sepsis due to surgical or traumatic incident, chronic renal failure, AIDs, cachexia and autoimmune conditions such as lupus erthyromatosis, host graft rejection and graft versus host disease.

SUMMARY OF THE INVENTION

In one aspect, the invention relates to p38beta2 polypeptides and recombinant materials and methods for their production. Another aspect of the invention relates to methods for using such p38beta2 polypeptides and polynucleotides. Such uses include the treatment of central nervous system disorder such as senile dementia of the Alzheimer's type (SDAT), multiple sclerosis, cerebral malaria, stroke, head trauma and spinal cord injury, cardiovascular diseases such as restonosis and atherosclerosis; inflammatory diseases such as Adult Respiratory Disease Syndrome (ARDS), Rhematoid arthritis, Osteoarthritis, Inflammatory Bowel Disease (IBD), psoriasis, dermatitis, asthma; and other such diseases or conditions associated with dysregulated or excess cytokines such as osteoporosis, sepsis due to surgical or traumatic incident, chronic renal failure, AIDs, cachexia and autoimmune conditions such as lupus erthyromatosis, host graft rejection and graft versus host disease, among others. In still another aspect, the invention relates to methods to identify agonists and antagonists using the materials provided by the invention, and treating conditions associated with p38beta2 imbalance with the identified compounds. Yet another aspect of the invention relates to diagnostic assays for detecting diseases associated with inappropriate p38beta2 activity or levels.

DESCRIPTION OF THE DRAWINGS

The FIGURE shows the nucleotide and deduced amino acid sequence from a human p38beta2. SEQ ID NOS:1 and 2.

DESCRIPTION OF THE INVENTION

Definitions

The following definitions are provided to facilitate understanding of certain terms used frequently herein.

"p38beta2" refers, among others, generally to a polypeptide having the amino acid sequence set forth in SEQ ID NO:2 or an allelic variant thereof.

"p38beta2 activity or p38beta2 polypeptide activity" or "biological activity of the p38beta2 or p38beta2 polypeptide" refers to the metabolic or physiologic function of said p38beta2 including similar activities or improved activities or these activities with decreased undesirable side-effects. Also included are antigenic and immunogenic activities of said p38beta2.

"p38beta2 gene" refers to a polynucleotide having the nucleotide sequence set forth in SEQ ID NO:1 or allelic variants thereof and/or their complements.

"Antibodies" as used herein include polyclonal and monoclonal antibodies, chimeric, single chain, and humanized antibodies, as well as Fab fragments, including the products of an Fab or other immunoglobulin expression library.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein.

"Polynucleotide" generally refers to any polyribonucleotide or polydeoxribonucleotide, which may be unmodified RNA or DNA or modified RNA or DNA. "Polynucloetides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as olignonucleotides.

"Polypeptide" refers to any peptide or protein comprising two or more amino acids joined to each other by peptide bonds or modified peptide bonds, i.e., peptide isoteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, gylcosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, PROTEINS-STRUCTURE AND MOLECULAR PROPERTIES, 2nd Ed., T. E. Creighton, W. H. Freeman and Company, New York, 1993 and Wold, F., Posttranslational Protein Modifications: Perspectives and Prospects, pgs. 1–12 in POSTTRANSLATIONAL COVALENT MODIFICATION OF PROTEINS, B. C. Johnson, Ed., Academic Press, New York, 1983; Seifter et al., "Analysis for protein modifications and nonprotein cofactors", *Meth Enzymol* (1990) 182:626–646 and Rattan et al., "Protein Synthesis: Posttranslational Modifications and Aging", *Ann NY Acad Sci* (1992) 663:48–62.

"Variant" as the term is used herein, is a polynucleotide or polypeptide that differs from a reference polynucleotide or polypeptide respectively, but retains essential properties. A typical variant of polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mustagenesis techniques or by direct synthesis.

"Identity" is a measure of the identity of nucleotide sequences or amino acid sequences. In general, the sequences are aligned so that the highest order match is obtained. "Identity" per se has an art-recognized meaning and can be calculated using published techniques. See, e.g.: (COMPUTATIONAL MOLECULAR BIOLOGY, Lesk, A. M., ed., Oxford University Press, New York, 1988; BIOCOMPUTING: INFORMATICS AND GENOME PROJECTS, Smith, D. W., ed., Academic Press, New York, 1993; COMPUTER ANALYSIS OF SEQUENCE DATA, PART I, Griffin A. M., and Griffin, H. G., eds., Humana Press, New Jersey, 1994; SEQUENCE ANALYSIS IN MOLECULAR BIOLOGY, von Heinje, G., Academic Press, 1987; and SEQUENCE ANALYSIS PRIMER, Gribskov, M. and Devereux, J., eds., M Stockton Press, New York, 1991). While there exist a number of methods to measure identity between two polynucleotide or polypeptide sequences, the term "identity" is well known to skilled artisans (Carillo, H., and Lipton, D., *SIAM J Applied Math* (1988)48:1073). Methods commonly employed to determine identity or similarity between two sequences include, but are not limited to, those disclosed in Guide to Huge Computers, Martin J. Bishop, ed., Acadmeic Press, San Diego, 1994, and Carillo, H., and Lipton, D., *SIAM J Applied Math* (1988) 48:1073. Methods to determine identity and similarity are codified in computer programs. Preferred computer program methods to determine identity and similarity between two sequences include, but are not limited to, GCS program package (Devereux, J., et al, *Nucleic Acids Research* (1984) 12(1):387), BLASTP, BLASTN, FASTA (Atschul, S. F. et al., *J Molec Biol* (1990) 215:403).

Polypeptides of the Invention

In one aspect, the present invention relates to p38beta2 polypeptides. The p38beta2 polypeptides include the polypeptide of SEQ ID NO:2; as well as polypeptides comprising the amino acid sequence of SEQ ID NO:2; and polypeptides comprising the amino acid sequence which have at least 80% identity to that of SEQ ID NO:2 over its entire length, and still more preferably at least 90% identity, and even still more preferably at least 95% identity to SEQ ID NO:2. Also included within p38beta2 polypeptides are polypeptides having the amino acid sequence which have at least 80% identity to the polypeptide having the amino acid sequence of SEQ ID NO:2 over its entire length, and still more preferably at least 90% identity, and still more preferably at least 95% identity to SEQ ID NO:2. Preferably p38beta2 polypeptide exhibit at least one biological activity of p38beta2.

The p38beta2 polypeptides may be in the form of the "mature" protein or may be a part of a larger protein such as fusion protein. It is also advantageous to include an additional amino acid sequence which contains secretory or leader sequences, pro-sequences, sequences which aid purification such as multiple histidine residues, or an additional sequence for stability during recombinant production.

Biologically active fragments of the p38beta2 polypeptides are also included in the invention. A fragment is a polypeptide having an amino acid sequence that entirely is the same as part, but not all, of the amino acid sequence of the aforementioned p38beta2 polypeptides. As with p38beta2 polypeptides, fragments may be "free-standing", or comprised within a larger polypeptide of which they form a part or region, most preferably as a single continuous region. Representative examples of polypeptide fragments of the invention, include, for example, fragments from about amino acid number 1–20, 21–40, 41–60, 61–80 , 81–100, and 101 to the end of p38beta2 polypeptide. In this context "about" includes the particularly recited ranges larger or smaller by several, 5, 4, 3, 2 or 1 amino acid at either extreme or at both extremes.

Preferred fragments include, for example, truncation polypeptides having the amino acid sequence of p38beta2 polypeptides, except for deletion of a continuous series of residues that includes the amino terminus, or a continuous series of residues that includes the carboxyl terminus or deletion of two continuous series of residues, one including the amino terminus and one including the carboxyl terminus. Also preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic region, flexible regions, surface-forming regions, substrate binding regions, and high antigenic index regions. Biologically active fragments are those that mediate p38beta2 activity, including those with a similar activity or an improved activity, or with a decreased undesirable activity. Also included are those that are antigenic or immunogenic in an animal, especially in a human.

Preferably, all of these polypeptide fragments retain the biological activity of the p38beta2, including antigenic activity. Variants of the defined sequence and fragments also form part of the present invention. Preferred variants are those that vary from the referents by conservative amino acid substitutions—i.e., those that substitute a residue with another of like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr. Particularly preferred are variants in which several, 5–10, 1–5, or 1–2 amino acids are substituted, deleted, or added in any combination.

The p38beta2 polypeptides of the invention can be prepared in any suitable manner. Such polypeptides include isolated naturally occurring polypeptides, recombinatly produced polypeptides, synthetically produced polypeptides, or polypeptides produced by a combination of these methods. Means for preparing such polypeptides are well understood in the art.

Polynucleotides of the Invention

Another aspect of the invention relates to p38beta2 polynucleotides, p38beta2 polynucleotides include isolated polynucleotides which encode the p38beta2 polypeptides and fragments, and polynucleotides closely related thereto. More specifically, p38beta2 polynucleotide of the invention include a polynucleotide comprising the nucleotide sequence set forth in SEQ ID NO:1 encoding a p38beta2 polypeptide of SEQ ID NO:2, and polynucleotide having the particular sequence of SEQ ID NO:1 p38beta2 polynucleotides further include a polynucleotide comprising a nucleotide sequence that has at least 80% identity to a nucleotide sequence encoding the 38beta2 polypeptide of SEQ ID NO:2 over its entire length, and a polynucleotide that is at least 80% identical to that having SEQ ID NO:1 over its entire length. In this regard, polynucleotides at least 80% identical are particularly preferred, and those with at least 95% are especially preferred. Furthermore, those with at least 97% are highly preferred and those with at least 98–99% are most highly preferred, with at least 99% being the most preferred. Also included under p38beta2 polynucleotides are a nucleotide sequence which has sufficient identity to a nucleotide sequence contained in SEQ ID NO:1 to hybridize under conditions useable for amplification or for use as a probe or marker. The invention also provides polynucleotides which are complementary to such p38beta2 polynucleotides.

p38beta2 of the invention is structurally related to other proteins of the CSBP/p38 MAP Kinases, as shown by the results of sequencing the cDNA encoding human p38beta2. The cDNA sequence contains an open reading frame encoding a polypeptide of 364 amino acids. Amino acid of sequence of the Figure (SEQ ID NO:2) has about 87.4% identity (using FASTA) in 364 amino acid residues with p38beta (Y. Ziange et al., J. Biol. Chem. 271: 17920–17926, 1996). Furthermore, p38beta2 is 75.5% identical to CSBP/p38 over 351 amino acid residues (J. C. Lee et al., Nature 372:739–746, 1994) Nucleotide sequence of the Figure ((SEQ ID NO:1) has about 84.1% identity (using FASTA) in 1073 nucleotide residues with p38beta (Y. Ziang et al., J. Biol. Chem. 271: 17920–17926, 1996). Furthermore, p38beta 2 is 69.6% identical to CSBP/p38 over 1032 nucleotide residues (J. C. Lee et al., Nature 372:739–746, 1994)

One polynucleotide of the present invention encoding p38beta2 may be obtained using standard cloning and screening, from a cDNA library derived from mRNA in cells of human brain, heart and sketal muscle using the expressed sequence tag (EST) analysis (Adams, M. D., et al. *Science* (1991) 252:1651–1656; Adams, M. D. et al., *Nature*, (1992) 355:632–634; Adams, M. D., et al., *Nature* (1995) 377 Supp:3–174). Polynucleotides of the invention can also be obtained from natural sources such as genomic DNA libraries or can be synthesized using well known and commercially available techniques.

The nucleotide sequence encoding p38beta2 polypeptide of SEQ ID NO:2 may be identical over its entire length to the coding sequence set forth in the figure (SEQ ID NO:1), or may be a degenerate form of this nucleotide sequence encoding the polypeptide of SEQ ID NO:2, or may be highly identical to a nucleotide sequence that encodes the polypeptide of SEQ ID NO:2. Preferably, the polynucleotides of the invention comprise a nucleotide sequence that is highly identical, at least 80% identical, with a nucleotide sequence encoding a p38beta 2 polypeptide, or at least 80% identical with the sequence contained in the figure (SEQ ID NO: 1) encoding p38beta2 polypeptide, or at least 80% identical to a nucleotide sequence encoding the polypeptide of SEQ ID NO:2.

When the polynucleotide of the invention are used for the recombinant production of p38beta2 polypeptide, the polynucleotide may include the coding sequence for the mature polypeptide or a fragment thereof, by itself; the coding sequence for the mature polypeptide or fragment in reading frame with other coding sequences, such as those encoding a leader or secretory sequence, a pre-, or pro- or protein sequence, or other fusion peptide portions. For example, a marker sequence which facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al, *Proc Natl Acad Sci USA* (1989) 86:821–824, or is an HA tag. The polynucleotide may also contain non-coding 5' an 3' sequences, such as transcribed, non-translated sequences, splicing and polyadenylation signals, ribosome binding sites and sequences that stabilize mRNA.

Further preferred embodiments are polynucleotides encoding p38beta2 variants comprise the amino acid sequence p38beta2 polypeptide of the figure (SEQ ID NO:2) in which several, 5-10, 1-5, 1-3, 1-2 or 1 amino acid residues are substituted, deleted or added, in any combination.

The present invention further relates to polynucleotides that hybridize to the herein above-described sequences. In this regard, the present invention especially relates to polynucleotides which hybridize under stringent conditions to ther herein above-described polynucleotides. As herein used, the term "stringent conditions" means hybridization will occur only if there is at least 95% and preferably at least 97% identity between the sequences.

Polynucleotides of the invention, which are identical or sufficiently identical to a nucleotide sequence contained in SEQ ID NO1, may be used as hybridization probes for cDNA and genomic DNA, to isolate full-length cDNAs and genomic clones encoding p38beta2 polypeptide and to isolate cDNA and genomic clones of other genes that have a high sequence similarity to the p38beta2 gene. Such hybridization techniques are known to those of skill in the art. Typically these nucleotide sequences are 70% identical, preferably 80% identical, more preferably 90% identical to that of the referent. The probes generally will comprise at least 15 nucleotides. Preferably, such probes will have at least 30 nucleotides and may have at least 50 nucleotides. Particularly preferred probes will range between 30 and 50 nucleotides.

In one embodiment, to obtain a polynucleotide encoding p38beta2 comprises the steps of screening an appropriate library under stringent hybridization conditions with a labeled probe having the SEQ ID NO:1 or a fragment thereof; and isolating full-length cDNA and genomic clones containing said polynucleotide sequence. Such hybridization techniques are well known to those of skill in the art. Stringent hybridization conditions are as defined above or alternatively conditions under overnight incubation at 42° C. in a solution comprising: 50% formamide, 5×SSC (150 mM NaCl, 15 mM trisodium citrate), 50 m M sodium phosphate (pH 7.6), 5×Denhardt's solution, 10% dextran sulfate, and 20 microgram/ml denatured, sheared salmon sperm DNA, followed by washing the filters in 0.1×SSC at about 65° C.

The polynucleotides and polypeptides of the present invention may be employed as research reagents and materials for discovery of treatments and diagnostics to animal and human disease.

Vectors, Host Cells, Expression

The present invention also relates to vectors which comprise a polynucleotide or polynucleotides of the present invention, and host cells which are genetically engineered with vectors of the invention and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis et al., BASIC METHODS IN MOLECULAR BIOLOGY (1986) and Sambrook et al., MOLECULAR CLONING: A LABORATORY MANUAL, 2nd Ed., Cold spring Harbor Laboratory Press, Cold Spring Harbor, N.Y. (1989) such as calcium phosphate transfection, DEAE-dextran mediated transfection, transvection, microinjection, cationic lipid-mediated transfection, electroporation, transduction, scrape loading, ballistic introduction or infection.

Representative examples of appropriate hosts include bacterial cells, such as streptococci, staphylococci, *E. coli, Streptomyces* and *Bacillus subtillis* cells: fungal cells, such as yeast cells and *Aspergillus* cells; insect cells such as *Drosophila* S2 and *Spodoptera* Sf9 cells : animal cells such as CHO, COS, HeLa, C127, 3T3, BHK, 293 and Bowes melanoma cells; and plant cells.

A great variety of expression systems can be used. Such systems include, among others, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector suitable to maintain, propagate or express polynucleotides to produce a polypeptide in a host may be used. The appropriate nucleotide sequence may be inserted into an expression sytem by any of a variety of well-known and routine techniques, such as, for example, those set forth in Sambrook et al., MOLECULAR CLONING, A LABORATORY MANUAL (supra).

For secretion of the translated protein into the lumen of the endoplasmic reticulum, into the perplasmic space or into the extracelluar environment, appropriate secretion signals may be incorporated into the desired polypeptide. These signals may be endogenous to the polypeptide or that may be heterologous signals.

If the p38beta2 polypeptide is expressed for use in screening assays, generally, it is preferred that the polypeptide to be produced at the surface of the cell. In this event, the cells may be harvested prior to use in the screening assay. If p38beta2 polypeptide is secreted into the medium, the medium can be recovered in order to recover and purify the polypeptide; if produced intracellularly, the cells must first be lysed before the polypeptide is recovered. p38beta2 polypeptides can be recovered and purified from recombinant cell cultures by well-known methods including ammonium sulfate or ethanol precipitation, acid extration, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be empolyed to regenerate active conformation when the polypeptide is denatured during isolatin and or purification.

Diagnostic Assays

This invnetion also relates to the use of p38beta2 polynucleotides for use as a diagnostic reagents. Detection of a mutated form of p38beta2 gene assocated with a dysfunction will provide a diagnostic tool that can add or define a diagnosis of a disease or susceptibility to a disease which results from under-expression, over-expression or altered expression of p38beta2. Individuals carrying mutations in the p38beta2 gene may be detected at the DNA level by a variety of techniques.

Nucleic acids for diagnosis may be obtained from a subject's cells, such as from blood, urine, saliva, tissue biopsy or autopsy material. The genomic DNA may be used directly for detection or may be amplified enzymatically by using PCR or other amplification technques prior to analysis. RNA or cDNA may also be used in similar fashion. Deletions and insertions can be detected by a change in size of the amplified product in comparision to the normal genotype. Point mutations can be identified by hybridizing amplified DNA to labeled p38beta2 nucleotide sequences. Perfectly matched sequences can be distinguished from mismatched duplexes by RNase digestion or by differences in melting temperatures. DNA sequence differences may also be detected by alterations in electrophoretic mobility of DNA fragments in gels, with or without dentauring agents, or by direct DNA sequencing. See, eg., Myers et al., *Science* (1985) 230:1242. Sequence changes at specific locations may also be revealed by nuclease protection assays, such as RNase and S1 protection or the chemical cleavage methods. See Cotton et al., *Proc Natl Acad Sci USA* (1985) 85:4387–4401. In another embodiment, an array of oligo-nucleotides probes comprising p38beta2 nucletodie sequence or fragments thereof can be constructed to conduct efficient screening of e.g., genetic mutations. Array technology methods are well known and have general applicability and can be used to address a variety of questions in molecular genetics including gene expression, genetic linkage, and genetic variability. (See for example: M. Chee et al., Science, Vol 274, pp 610–613 (1996)).

The diagnostic assays offer a process for diagnosing or determining a susceptibility to central nervous system disorder such as senile dementia of the Alsheimer's type (SDAT), multiple sclerosis, cerebral malaria, stroke, head trauma and spinal cord injury; cardiovascular diseases such as restenosis and atherosclerosis; inflammatory diseases such as Adult Respriatory Disease Syndrome (ARDS), Rheumatoid arthiritis, Osteoarthritis, Inflammatory Bowel Disease (IBD), psoriasis, dermatitis, asthama; and other such diseases or conditions associated with dysregulated or excess cytokines such as osteoporosis, sepsis due to surgical or traumatic incident, chronic renal failure, AIDs, cachexia and autoimmune conditions such as lupus erthyromatosis, host graft rejection and graft verus disease through detection of mutation in the p38beta2 gene by the methods described.

In addition, central nervous system disorder such as senile dementia of the Alzheimer's type (SDAT), mutiple sclerosis, cerebral malaria, stroke, head trauma and spinal cord injury; cardiovascular diseases such as restenosis and atherosclerosis; inflammatory diseases such as Adult Respiratory Disease Syndrome (ARDS), Rheumatoid arthritis, Osteoarthritis, Inflammatory Bowel Disease (IBD), psoriasis, dermatitis, asthma; and other such diseases or conditions associated with dysregulated or excess cytokines such as osteoporosis, sepsis due to surgical or traumatic incident, chronic renal failure, AIDs, cachexia and autoimmune conditions such as lupus erthyromatosis, host graft rejection and graft verus host disease, can be diagnosed by methods comprising determining from a sample derived from a subject an abnormally decreased or increased level of p38beta2 polypeptide or p38beta2 mRNA. Decreased or increased expression can be measured at the RNA level using any of the methods well known in the art for the quantitation of polynucleotides, such as, for example, PCR, RT-PCR, RNase protection. Northern blotting and other hybridization methods. Assay techniques that can be used to determine levels of a proteins, such as an p38beta2 polypeptide, in a sample derived from a host are well-known to those of skill in the art. Such assay methods includ radioimmunoassays, competitive-binding assays, Western Blot analysis and ELISA assays.

Chromosome Assays

The nucleotide sequences of the present invention are also valuable for chromosome identification. The sequence is specfically targeted to and can hybridize with a particular location on an individual human chromosome. The mapping of relevant sequences to chromosomes according to the present invention is an important first step in correlating these sequences with gene associated disease. Once a sequence has been mapped to a precise chromosomal location, the physical position of the sequence on the chromosome can be correlated with genetic map data. Such data are found, for example, In V. McKusick, Mendelian Inheritance in Man (available on line through John Hopkins University Welch Medical Library). The relationship between genes and diseases that have been mapped to the same chromosomal region are then identified through linkage analysis (coinheritance of physically adjacent genes).

The differences in the cDNA or genomic sequence between affected and unaffected individuals can also be determined. If a mutation is observed in some or all of the affected individuals but not in any normal individuals, then the mutation is likely to be the causative agent of the disease.

Antibodies

The polypeptides of the invention or their fragments or analogs thereof, or cells expressing them can also be used as immunogens to produce antibodies immunospecific for the p38beta2 polypeptides. The term "immunospecific" means that he antibodies have subtantial greater affinity for the polypeptides of the invention than their affinity for other related polypeptides in the prior art.

Antibodies generated against the p38beta2 polypeptides can be obtained by administering the polypeptides or epitope-bearing fragments, analogs or cells to an animal, preferably a nonhuman, using routine protocols. For preparation of monoclonal antibodies, any technique which provides antibodies produced by continuous cell line cultures can be used. Examples include the hybridoma techniq (Kohler, G. and Milstein, C., Nature (1975) 256:495–497), the trioma technique, the human B-cell hybridoma technique (Kozbor et al., Immunology Today (1983) 4:72) and the EBV-hybridoma technique (Cole et al., MONOCLONAL ANTIBODIES AND CANCER THERAPY, pp. 77–96Alan R. Liss, Inc. 1985).

Techniques for the production of single chain antibodies (U.S. Pat. No 4,946,778) can also be adpated to produce single chain antibodies to polypeptides of this invention. Also, transgenic mice, or other organims including other mammals, may be used to express humanized antibodies.

The above-described antibodies may be employed to isolate or to identify clones expressing the polypeptide or to purify the polypeptides by affinity chromatography.

Antibodies against p38beta2 polypeptides may also be employed to treat central nervous system disorder such as senile dementia of the Alzheimer's type (SDAT), multiple sclerosis, cerebral malaria, stroke, head trauma and spinal cord injury; cardiovascular diseases such as restenosis and atherosclerosis; inflammatory diseases such as Adult Respiratory Disease Syndrome (ARDS), Rheumatoid arthritis, Osteoarthritis, Inflammatory Bowel Disease (IBD), psoriasis, dermatitis, asthma; and othe such diseases or conditions associated with dysregulated or excess cytokines such as asteporosis, sepsis due to surgical or traumatic incident, chronic renal failure, AIDs, cachexia and autoimmune conditions such as lupus erthyromatosis, host graft rejection and graft versus host disease, among others.

Vaccines

Another aspect of the invention relates to a methods for inducing an immunological response in a mammal which comprises inoculating the mammal with p38beta2 polypeptide, or a fragment thereof, adequate to produce antibody and/or T cell immune response to protect said animal from central nervous system disorder such as senile dementia of the Alzheimer's type (SDAT), multiple sclerosis, cerebral malaria, stroke, head trauma and spinal cord injury; cardiovascular diseases such as restenosis and atherosclerosis; inflammatory diseases such as Adult Respiratory Disease Syndrome (ARDS), Rheumatoid arthritis, Osteoarthritis, Inflammatory Bowel Disease (IBD), psoriasis, dermatitis, asthma; and other such diseases or conditions associated with dysregulated or excess cytokines such as osteporosis, sepsis due to surgical or traumataic incident, chronic renal failure, AIDs, cachexia and autoimmune conditions such as lupus erthyromatosis, host graft rejection and graft versus host disease, among others. Yet another aspect of the invention relates to a methods of inducing innunological response in a mammal which comprises, delivering p38beta2 polypeptide via a vector directing expression of p38beta2 polynucleotide in vivo in order to induce such an immunological response to produce antibody to protect said animal from diseases.

Further aspect of the invention relates to an immunological/vaccine formulation (composition) which, when introduced into a mammalian host, induces an immunological response in that mammal to a p38beta2 polypeptide wherein the composition comprises a p38beta2 polypeptide or p38beta2 gene. The vaccine formulation may further comprise a suitable carrier. Since p38beta2 polypeptide may be broken down in the stomach, it is preferable administered parenterally (including subcutaneous, intramuscular, intravenous, intradermal etc. injection). Formulations suitable for parenteral administration include aqueous and non-aqueous sterile injection solutions which may contain antioxidants, buffers, bacteristats and solutes which render the formulation instonic with the blood if the recipient; and aqueous and non-aquous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Screening Assays

The p38beta2 polypeptide of the present invention may be employed in a screening process for compounds which activate (agonists) or inhibit activatgion of (antagonists, or otherwise called inhibitors) the p38beta2 polypeptide of the present inention. Thus, polypeptides of the invention may also be used to assess identify agonist or antagonists from, for exampke, cells, cell-free preparations, chemical libraries, and natural product mixtures. These agonists or antagonists may be natural substrates, ligands, receptors, etc., as the case may be, of the polypeptide of the present invention; or may be structural or functional mimetics of the polypeptide of the present invention. See Coligan et al., *Current Protocols in Immunology* (1(2): Chapter 5(1991).

p38beta2 polypeptides are ubiquitous in the mammalian host and are responsible for many biological functions, including pathologies. Accordingly, it is desirous to find compounds and drugs which stimulate p38beta2 polypeptide on the one hand and which can inhibit the function of p38beta2 polypeptide on the other hand. In general, agonists are employed for therapeutic and prophylactic purposes for such conditions as central nervous system disorder such as senile dementia of the Alzheimer's type (SDAT), mutiple sclerosis, cerebral malaria, stroke, head trauma and spinal cord injury; cardiovascular diseases such as restenosis and atherosclerosis; inflammatory diseases such as Adult Respiratory Disease Syndrome (ARDS), Rheumatoid arthritis, Osteoarthritis, Inflammatory Bowel Disease (IBD), psoriasis, dermatitis, asthma; and other such diseases or conditions associated with dysregulated or excess cytokines such as osteoporosis, sepsis due to surgical or traumatic incident, chronic renal failure, AIDs, cachexia and autoimmune conditions such as lupus erthyromatosis, host graft rejection and graft versus host disease. Antagonists may be employed for a variety of therapeutic and prophylactic purposes for such condidtions as central nervous system disorder such as senile dementia of the Alzheimer's type (SDAT), mutiple sclerosis, cerebral malaria, stroke, head trauma and spinal cord injury; cardiovascular diseases such as restenosis and atherosclerosis; inflammoatory diseases such as Adult Respiratory Disease Syndrome (ARDS), Rheumatoid arthritis, Osteoarthritis, Inflammatory Bowel Disease (IBD), psoriasis, dermatitis, asthma; and other such diseases or conditions associated with dysregulated or excess cytokines such as osteoporosis, sepsis due to surgical or traumatic incident, chronic renal failure, AIDs, cachexia and autoimmune conditions such as lupus erthyromatosis, host graft rejection and graft versus host disease.

In general, such screening procedures may involve using appropriate cells which express the p38beta2 polypeptide or respond to p38beta2 polypeptide of the present invention. Such cells include cells from mammals, yeast, *Drosophilia* or *E. coli*. Cells which express the p38beta2 polypeptide (or cell membrane containing the expresses polypeptide) or respond to p38beta2 polypeptide are then contacted with a test compound to observe binding, or stimulation or inhibition of a functional response. The ability of the cells which were contacted with the candidate compounds is compared with the same cells which wre not contacted for p38beta2 activity.

This invention also provides a method for determining wheter a ligand previously not known to bind to a p38beta2 can bind to such as protein. The method comprises contacting the ligand to be identified with cytosolic fraction from mammalian cells and measuring its ability to compete with a known radioactive CSAID, in a CSAIDs binding assay (Lee et. al Nature 372:739–746; and previous CSBP filings). Alternatively, the purified recombinant protein could be used to substitute for crude THP.1 cell lysates in a competitive binding assay with a CSAID such as SB 202190 or a related compound (Lee et al., Nature 372:739–746).

The knowledge that the p38beta encodes protein kinases suggests that recombinant forms can be used to establish a protein kinase activity. Typically this would involve the direct incubation of p38beta2 with a protein or peptide substrate in the presence of $\gamma$-$^{32}$p. ATP, followed by the measurement of radioactivity incorporated into the substrate by separtion and counting. Separation methods include immunoprecipitation, conjugation of substrate to a bead allowing separation by centrigugation or determination of incorporation by scintillation proximity assay, SDS-PAGE followed by autoradiography or biosensor analysis. While the specific substrates are not yet known, candidates include p38beta2 itself (autophosphorylation), myelin basic protein, ATF2, MAPKAP kinase-2, MAPKAP kinase-3 (see McLaughlin et al., (1996) J. Biol. Chem. 271:8488–8492 and reference therein) and peptides related to known MAP kinase substrates. Other substances might be discovered by incubating p38beta2 with random peptides conjugated to solid supports or displayed on the surface of phage or by incubation of p38beta2 with mammalian cell lysates (e.g. THP.1 cell lysates) and $\gamma$-$^{32}$P. ATP, followed by separation of the labelled target proteins, and sequencing. Kinase activity may also be detected by use of antiphosphotyrosine antibodies. The protein kinase activity of p38beta2 may require incubation with a specific MAP kinase kinase. This may be achieved by preincubating P38beta2 with lysates from stimulated eukaryotic cells (e.g., LPS treated THP.1 cells) and ATP. Alternatively, it may be possible to isolate a more active form of p38beta2 from HOG1deletion strains of yeast expressing the human p38beta2 and grown in high osmolarity conditions (see, for example, Kumar et al., (1995) J. Biol. Chem. 270:29043–29046).

These assays permit the discovery and modification of compounds which inhibit p38beta2 kinase activity in vitro, a known property of CSAIDS (Lee, et al., *Nature*, supra). Such compounds will block cytokine synthesis in a comparable fashion to the compounds described herein. They could also lead to the discovery of novel substrates which themselves may be viable targets for discovery of novel compounds which block cytokine production.

It is expected that p38beta2, like other MAP kinase, will be activated by a MAP kinase kinase, hence the recombinant protein would allow the establishment of a second assay which measures the ability of p38beta 2 to be phosphorylated by putative MAP kinase kinases. In this case fractions from stimulated cell lysates (eg THP.1 cells stimulated with LPS) are incubated with p38beta2 in the presence of $\gamma$-$^{32}$P-ATP, and the incorporation of $^{32}$P-label into p38beta2 measured by separation and counting. Also, tyrosine phsophorylation of p38beta2 could be detected by immunoprecipitation or immunoblot with commercially available anti-phosphotyrosine antibodies.

These assays can be used to discover compounds which block the activation of p38beta2 protein kinase activity and to improve the potency of already discovered compounds. These compounds would be expected to have utility due to their blocking of cytokine synthesis..

The ability of human p38beta2 to rescue to HOG1 deletion strain upon growth in conditions of high osmolarity allows for the direct screening of compounds which block p38beta2 activity in vivo. For example, compounds could be screened for their ability to block growth of a p38beta2 +/HOG1-yeast strain in high osmolarity but which have no effect on growth of the same strain in standard osmolarity or on a p38beta2-/HOG1+ in high osmolarity. The sensitivity of the yeast based assay can be increased by introducing host mutations that affect the cell membrane and permeability (Gaber, et al., *Mol. Cell. Bio.* 9:3447–3456. (1989)).

The discovery that the p38beta2 of this invention is homologous to the CSBP/P38 MAP kinase family of serine-threonine protein kinases provides a specific rationale for the treatment of a wide variety of acute and chronic inflammatory diseases. Accordingly, it is a further aspect of this invention to treat patients suffering from the effects of cytokine-mediated inflammatory disease with a p38beta2 inhibitory amount of CSAID. Illustrative examples of such diseases include, without limitation, disease associated with the central nervous system such as senile dementia of the Alzheimer's type (SDAT), multiple sclerosis, cerebral malaria, stroke, head trauma and spinal cord injury; cardiovascular diseases such as restenosis and atheroscleoris; inflammatory diseases such as Adult Respiratory Disease Syndrome (ARDS), Rheumatoid arthritis, Osteoarthritis, Inflammatory Bowel Disease (IBD), psoriasis, dermatitis, asthma; and other such diseases or conditions associated with dysregulated or excess cytokines such as osteporosis, sepsis due to surgical or traumatic incident, chronic renal failure. AIDs, cachexia and autoimmune conditions such as lupus erthyromatosis, host graft rejection and graft verus host disease. Thus this invention contemplates the treatment and/or amelioration of such disease by administering a p38beta2 inhibiting amount of a compound. Without wishing to be bound by any particular theory of the functioning of the p38beta2 of this invention, it is believed that amoung the useful inhibitors of p38beta2 function are those compounds which inhibit the kinase activity of the p38beta2. Other sites of inhibition are, of course, possible owing to its position in a signal transduction cascasde. Therefore, inhibiting the interaction of p38beta2 with one or more of its upstream or downstream substrates is also contemplated by this invention.

The assays may simple test binding of a candidate compound wherein adherence to the cells bearing the p38beta2 polypeptide is detected by means of a label directly or indirectly associated with the candidate compound or in an assay involving competition with a labeled competitor. Further, these assays may test whether the candidate compound results in a signal generated by activation of the p38beta2 polypeptide, using detection systems appropriate to the cells bearing the p38beta2 polypeptide. Inhibitors of activation are generally assayed in the presence of a known agonist and the effect on activation by the agonist by the presence of the candidate compound is observed. Standard methods for conducting such screening assays are well understood in the art.

Examples of potentional p38beta2 polypeptide agtagonists include antibodies or, in some cases, oligonucleotides or proteins which are closely related to the ligands, substrates, receptors, etc., as the case may be, of the p38beta2 polypeptide, e.g., a fragment of the ligands, substrates, receptors, or small molecules which bind to the polypeptide of the present invention but do not elicit a response, so that the acitivity of the polypeptide is prevented.

Prophylactic and Therapeutic Methods

This invention provides methods of treating an abnormal conditions related to both an excess of and insufficient amounts of p38beta2 polypetptide activity.

If the activity of p38beta2 polypeptide is in excess, several approaches are avaialbe. One approach comprises administering to a subject an inhibitor compound (antagonist) as hereinabove described along with a pharmaceutically acceptable carrier in an amount effective to inhibit activation by blocking binding of ligands to the p38beta2 polypeptide, or by inhibiting a second signal, and thereby alleviating the abnormal condition.

In another approach, soluble forms of p38beta2 polypeptides still capable of binding the ligand in competition with endogenous p38beta 2 polypeptide may be administered. Typical embodiments of such competitors comprise fragments of the p38beta2 polypeptide.

In still another approach, expression of the gene encoding endogenous p38beta2 polypeptide can be inhibited using expressin blocking techniques. Known such techniques involve the use of antisense sequences, either internally generated or separately administered. See, for example, O'Connor, *J Neurochem*(1991) 56:560 in *Oligodeoxynucleotides as Antisense Inhibitors of Gene Expression*, CRC Press, Boca Raton, Fla. (1988). Alternatively, oligonucleotides which form triple helices with the gene can be supplied. See, for example, Lee et al., *Nucleic Acids Res* (1979) 6:3073; Cooney et al., *Science* (1988) 241:456; Dervan et al., *Science* (1991) 251:1360. These oligomers can be administered per se or the relevant oligomers can be expressed in vivo.

For treating abnormal conditions related to an underexpression of p38beta2 and its activity, several approaches are also available. One approach comprises administering to a subject a therapeutically effective amount of a compound which activates p38beta2 polypeptide, i.e., an agonist as described above, in combination with a pharmaceutically acceptable carrier, to thereby alleviate the abnormal condition. Alternatively, gene therapy may be employed to effect the endogenous production of p38beta2 by the relevant cells in the subject. For example, a polynucleotide of the invention may be engineered for expression in a replication defective retroviral vector, as discussed above. The retroviral expression construct may then be isolated and introduced into a packaging cell tranduced with a retroviral plasmid vector containing RNA encoding a polypeptide of the present invention such that the packaging cell now produces infectious viral particles containing the gene of interest. These producer cells may be administered to a subject for engineering cells in vivo and expression of the polypeptide in vivo. For overview of gene therapy, see Chapter 20, *Gene Therapy and other Molecular Genetic-based Therapeutic Approaches*, (and references cited therein) in Human Molecular Genetics, T Strachan and A P Read, BIOS Scientific Publishers Ltd (1996).

Formulation and Administration

Peptides, such as the soluble form of p38beta2 polypeptides, agonists and antagonist peptides or small molecules, may be formulated in combination with a suitable pharmaceutical carrier. Such formulations comprise a therapeutically effective amount of the polypetptide or compound, and a pharmaceutically acceptable carrier or excipient. Such carriers include but are not limited to, saline, buffered saline, dextrose, water, glycerol, ethanol, and combinations thereof. Formulation should suite the mode of administration, and is well within the skill of the art. The invention further relates to pharmaceutical packs and kits comprising one or more containerrs filled with one or more of the ingredients of the aforementioned compositions of the invention.

Polypeptides and other compounds of the present invention may be employed alone or in conjunction with other compounds, such as therapeutic compounds.

Preferred forms of systemic administration of the pharmaceutical compositions include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if properly formulated in enteric or encapsulated formulations, oral administration may also be possible. Administration of these comopunds may also be topical and/or localized, in the form of salves, pastes, gels and the like.

The dosage range required depends on the choice of peptide, the route of administration, the nature of the formulation, the nature of the subject's condition, and the judgement of the attending practitioner. Suitable dosages, however, are in the range of 0.01–100 μg/kg of subject. Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

Polypeptides used in treatment can also be generated endogenously in the subject, in treatment modalities often referred to as "gene therapy" as described above. Thus, for example, cells from a subject may be engineered with a polynucleotide, such as a DNA or RNA, to encode a polypeptide ex vivo, and for example, by the use of a retroviral plasmid vector. The cells are then introduced into the subject.

EXAMPLES

The examples below are carried out using standard techniques, which are well known and routine to those of skill in the art, except where otherwise described in detail. The examples illustrate, but do not limit the invention.

Example 1-Cloning

One polynucleotide of the present invention encoding p38beta2 may be obtained using standard cloning and screening, from a cDNA library derived from mRNA in cells of human brain, heart, and skeletal muscle and using the polymerase chain reaction technique (M. A. Innis et al., PCR protocols: A guid to methods and application, Academic Press, San Diego, 1990). p38beta2 was cloned from a human brain cDNA library (LIFE TECHNOLOGY GeneTrapper library) by PCR using primers 5' GTG AAA TTC TGC TCC GGA C 3' (SEQ ID NO:3) and 5' ATC TCG AGA AGC TTT GCC CAG ACT CCT ACA CAT 3' (SEQ ID NO:4) based on the published p38beta2 sequence (Jiang, Y., Chen, C., Li, Z., Guo, W., Gegner, J. A., Lin, S., and Han, J. (1996) J. Biol. Chem. 271, 17920–17926).

Example 2

Tissue Distribution

A Northern blot was conducted with a p38beta2 cDNA on a human multiple tissue Northern from Clontech. Conditions used have been reported previously (Lee, J. C., Laydon, J. T., McDonnell, P. C., Gallagher, T. F., Kumar, S., Green, D., McNulty, D., Blumenthal, M. J., Heys, J. R., Landvatter, S. W., Strickler, J. E., Mc Laughlin, M. M., Siemens, I. R., Fisher, S. M., Livi, G.P., White, J. R., Adams, J. L., and Young, P. R. (1994) Nature 372, 739–746), p38beta2 was expressed most abundantly in human brain and heart with lower expression in placenta, lung, liver, skeletal muscle, kidney and pancreas.

Example 3

Homology to MAP Kinase Family and Expression p38beta2 may be engineered for yeast expression in a similar manner to that previously described for CSBP1 and CSBP2 (Kumar, S., McLaughlin, M. M., McDonnel, P. C., Lee, J. C., Livi, G. P., and Young, P. R. (1995) J. Biol. Chem. 270, 29043–29046). An XhoI and BglII site is engineered at the initiation and termination codon, respectively of p38beta2 by the polymerase chain reaction (Mullins and Faloona, Meth. Enymol. 155:335–50 (1987). An XhoI/BglII fragment containing p38beta2 is then ligated into the same sites in p138NBU, a modification of p138NB (McHale et al., Mol. Pharm. 39:109–113 (1991)) in which the Trp selectable marker is replaced with URA3. Alternatively, the amino terminus of p38beta2 can be fused to an epitope tag such as the FLAG epitope (for which reagents are available from IBI-Kodak) by using a polymerase chain reaction which includes an XhoI sire, the FLAG epitope and the amino terminal nucleotide sequence of p38beta2.

p38beta2 can also be engineered for expression in mammalian cells such as HeLa and JURKAT by fusing the amino terminus of p38beta2 with a FLAG or haernagglutinin (HA) epitope. An EcoRI/HindIII restriction fragment containing the complete open reading frame of human p38beta2 was excised from the PCR.2.1 plasmid it was originally cloned, and inserted into the vector pCDN cut with EcoRI and HindIII. The resulting vector pCDNHA-p38beta2 could then be transfected into mammalian cells such as HeLa or JURKAT using a number of established protocols, eg lipofectamine (GIBCO-BRL). Treatment of cells with a suitable stimulus (eg osmotic shock, UV, IL-1) leads to activation of the HA-p38beta2, and CSAID binding can be detected through the ability of CSAIDs to inhibit the kinase activity of p38beta2. Thus, HA-p38beta2 can be immunoprecipitated from transfected mammalian cells with antibodies to the HA epitope (Boeringer-Mannheim), and in vitro kinase assay can be performed with a suitable substrate (eg myelin basic protein, ATF-2, MAPKAP kinase-2 or 3) in the presence or absence of CSAID as previously described (Lee et al., (1994) Nature 372:739–746; McLaughlin et al., J. Biol. Chem. 271:8488–8492 (1996)).

Example 4

Expression in E. coli

To confirm that the proteins encoded by the isolated cDNAs of this invention can bind to CSAIDS, the cDNA may be expressed in E. coli, yeast and mammalian cells (e.g., HeLa, CHO, 3T3). In E. coli the CSBP/p38s are expressed as fusion proteins, for example, with β-galactosidase, an enterokinase cleavable FLAG epitope tag, gluthathione S-transferase or a hexaHistidine tail. (FLAG is a commercial epitope for which reagents are available through IBI-Kodak). In the latter case this is achieved by the design of a synthetic oligonucleotide linker with an initiation site, antibody recognition sequence, and enterokinase cleavage site. Proteins are expressed under the control of either the pLac (e.g., Bluescript KS vector from Stratagene, LaJolla, Calif.) or λpL (Shatzman, et al., N.Y. Acad. Sci., 478:233–248 (1986)) promoters and probed with a radiophotoaffinity CSAIDs shown to specifically crosslink proteins of the expected sized in cell lysates.

Protein expressed in E. coli is purified by passage over an affinity matrix containing a monoclonal antibody to the FLAG epitope, gluathione beads or a NiNTA column according to manufactur's instructions.

What is claimed is:

1. An isolated polypeptide comprising the amino acid sequence of SEQ ID NO:2.

2. An isolated polypeptide consisting of the amino acid sequence of SEQ ID NO:2.

3. An isolated polypeptide prepared by a process comprising culturing a host cell comprising an expression system capable of producing the polypeptide of SEQ ID NO:2 under conditions sufficient for the production of said polypeptide and recovering said polypeptide from the culture.

4. The isolated polypeptide of claim 3 wherein said expression system comprises the nucleotide sequence of SEQ ID NO:1.

* * * * *